US00PP17150P2

(12) United States Plant Patent
Austin

(10) Patent No.: US PP17,150 P2
(45) Date of Patent: Oct. 10, 2006

(54) SHRUB ROSE PLANT NAMED 'AUSTIGER'

(50) Latin Name: *Rosa hybrida*
Varietal Denomination: AUStiger

(75) Inventor: David C. H. Austin, Wolverhampton (GB)

(73) Assignee: David Austin Roses Ltd., Wolverhampton (GB)

( * ) Notice: Subject to any disclaimer, the term of this patent is extended or adjusted under 35 U.S.C. 154(b) by 0 days.

(21) Appl. No.: 11/033,946

(22) Filed: Jan. 11, 2005

(51) Int. Cl.
*A01H 5/00* (2006.01)

(52) U.S. Cl. ..... Plt./107

(58) Field of Classification Search ..... Plt./107, Plt./137, 148
See application file for complete search history.

(56) References Cited

U.S. PATENT DOCUMENTS

PP10,969 P * 6/1999 Austin ..... Plt./107

* cited by examiner

*Primary Examiner*—Howard J. Locker
(74) *Attorney, Agent, or Firm*—Klarquist Sparkman LLP

(57) ABSTRACT

Shrub rose plant having soft pink blooms, touched with apricot; flowers in the form of shallow, incurved cups; upright, bushy shrub growth; and light myrrh fragrance.

1 Drawing Sheet

Genus and species: *Rosa hybrida.*
Variety denomination: 'AUStiger'.

ORIGIN OF THE INVENTION

The present invention relates to a new and distinct variety of a shrub rose plant named 'AUStiger' which was originated by me by crossing an unnamed, unpatented seedling and the variety 'AUSpoly' (CHARLOTTE™), U.S. Plant Pat. No. 9,008.

BACKGROUND OF THE INVENTION

The primary objective of this breeding was to produce a very free flowering and healthy rose variety, having soft pink, cupped blooms on a narrow bushy shrub.

BRIEF SUMMARY OF THE INVENTION

The objective was subsantially achieved, along with other desirable improvements, as evidenced by the following unique combination of characteristics that are outstanding in the new variety and that distinguish it from its parents, as well as from all other varieties of which I am aware:

1. Soft pink blooms, touched with apricot.
2. Flowers in the form of shallow, incurved cups.
3. Upright, bushy shrub.
4. Light myrrh fragrance.

Asexual reproduction of this new variety by budding, as performed at Albrighton, England, shows that the foregoing and all other characteristics and distinctions come true to form and are established and transmitted through succeeding propagations.

COMPARISON WITH PARENTS

'AUStiger' has less petalage and more upright growth than the seed parent. The pollen parent 'AUSpoly' has large yellow blooms compared with the medium soft pink blooms of 'AUStiger'.

COMPARISON WITH SIMILAR VARIETY

'AUSland' (U.S. Plant Pat. No. 10,969) has soft pink blooms with less petalage than the apricot tinted blooms of 'AUStiger'. 'AUSland' has less upright growth than 'AUStiger'.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—Unnamed Seedling. (Unpatented).
*Pollen parent.*—'AUSpoly' (U.S. Plant Pat. No. 9,008).

FLOWER

Observations made from plants commencing at one year of age grown in a garden environment at Albrighton, England.

Blooming habit: Recurrent. The number of blooms per plant during the growing season is profuse.

Bud:
*Size.*—About 2.6 cm long and 1.6 cm in diameter when the petals start to unfurl.
*Form.*—The bud form is pointed ovoid.
*Color.*—When sepals first divide, bud color is Red Group 48B at the base shading to Orange-Red Group 34D at the top. When half blown, the upper sides of the petals are Orange-Red Group 31A; and the lower sides of the petals are Orange-Red Group 31B.

*Sepals.*—Color: Upper surface: Greyed-Purple Group 183A. Lower surface: Yellow-Green Group 146B. Length: 2.3 cm. Width: 0.9 cm. Shape: Subulate. Surface texture: Upper surface: Pubescent. Lower surface: Pubescent. There are three normally appendaged sepals. There are two unappendaged sepals with canescent edges.

*Receptacle.*—Color: Yellow-Green Group 144A, with Greyed-Orange Group 166A overlay before sepals unfurl. Shape: Funnel. Size: Medium, about 1.1 cm long×0.9 cm wide. Surface: Smooth.

*Peduncle.*—Length: Medium, averaging about 5 cm. Surface: Prickly. Color: Yellow-Green Group 144A, with Greyed-Orange Group 166A overlay on young growth. Strength: Strong.

Bloom:

*Size.*—Medium. Average open diameter is about 7.1 cm.

*Borne.*—Several together in irregular clusters of three to five blooms.

*Stems.*—Strength: Strong. Average length is about 30 cm with a diameter of 0.6 cm.

*Form.*—When first open: Cupped. Permanence: Retains its form to the end. Outer petal edges curl slightly.

*Petalage.*—Number of petals under normal conditions: 140.

*Color.*—The upper sides of the petals are Red Group 56C. The reverse sides of the petals are Red Group 56D. The base of each petal is Yellow Group 8B. The major color on the upper side is Red Group 56C.

*Variegations.*—None.

*Discoloration.*—The general tonality at the end of the first day: Red Group 56C. At the end of the third day: White Group N155D.

*Fragrance.*—Slight myrrh.

Petals:

*Texture.*—Smooth.

*Size.*—Width: 2.1 cm. Length: 3.2 cm.

*Surface.*—Smooth.

*Shape.*—Oval, notched. Margin: Slightly incurved. Inner petals undulating. Apex Shape: Emarginate. Base Shape: Pointed. Form: Incurved, tips of outer petals slightly recurved.

*Arrangement.*—Regularly arranged.

*Petaloids.*—Number: 3. Color: Yellow Group 12A.

*Persistence.*—Petals drop off cleanly before drying.

*Lastingness.*—On the plant: Short (about 2 days). As a cut flower: Short (about 2 days).

Reproductive parts:

*Stamens.*—Number: 5. Length: 4 mm. Anthers: Length: 1 mm. Color: Yellow-Orange Group 15A. Arrangement: Mixed with petaloids. Filaments: Color: Yellow-Orange Group 14B. Length: 3 mm. Pollen: Color: Yellow-Orange Group 15A.

*Pistils.*—Number: 37. Length: 6 mm. Styles: Color: Green Group 142D. Length: 5 mm. Stigmas: Color: Yellow-Orange Group 17A. Length: 1 mm. Hips: None observed.

PLANT

*Form.*—Shrub.

*Growth.*—Upright and of medium vigor.

*Age at maturity.*—Two years.

*Mature plant.*—Height: 1 m. Width: 0.75 m.

*Wood.*—Mature Stem: Average length: 39 cm. Average diameter: 6 mm. Internode distance: 65 mm. The above measurements are all variable, depending on growing conditions in a season.

*Rootstock.*—Dr. Huey in the United States. *Rosa dumetorum* 'Laxa' for the observed plants in the United Kingdom.

Foliage: Number of leaflets on normal mid-stem leaves: 7, including terminal leaflet.

*Size.*—Medium. About 15.8 cm long×8.3 cm wide.

*Quantity.*—Average number leaves per flowering stem: 6.

*Color.*—New foliage: Upper side: Yellow-Green Group 146A overlaid with Greyed-Purple Group 183B. Lower side: Yellow-Green Group 147B, overlaid with Greyed-Purple Group 183D. Old foliage: Upper side: Green Group 137A. Lower side: Yellow-Green Group 147B. Upper surfaces of new and old foliage are matte.

Leaflets:

*Size.*—About 4.5 cm long×3.5 cm wide.

*Shape.*—Elliptic.

*Base shape.*—Rounded.

*Apex shape.*—Cuspidate, leaflets becoming rounded as leaf matures.

*Texture.*—Smooth.

*Edge.*—Serrated.

*Serrations.*—Single and small.

*Petiole.*—Color: Green Group 143C.

*Petiole rachis.*—Color: Green Group 143C. Underside: Prickles and glands.

*Auricle shape.*—Subulate.

*Stipules.*—Length: 2 cm; bearded.

*Disease resistance.*—Resistant to mildew, blackspot and rust under normal growing conditions.

*Pest resistance.*—Not tested.

*Vein color.*—Yellow-Green Group 145B.

*Venation pattern.*—Reticulate.

Wood:

*New wood.*—Color: Greyed-Orange Group 166A. Bark: Smooth.

*Old wood.*—Color: Green Group 143A. Bark: Smooth.

Prickles:

*Quantity.*—On main canes from base: Few, 5 per 10 cm per stem length. On laterals from main canes: Few, 5 per 10 cm stem length.

*Form.*—Hooked downward.

*Length.*—9 mm.

*Color when young.*—Red Group 53B and Yellow-Green Group N144A.

*Color when mature.*—Grey-Brown Group 199D.

Small prickles:

*Quantity.*—On main stalks: Few, 4 per 10 cm of stem length. Toward the base of a stem the prickles are more densely arranged with 8–10 per 10 cm stem length. On laterals: Ordinary, 8 per 10 cm stem length.

*Color.*—When young: Yellow-Green Group N144A overlaid with Red Group 53B. When mature: Grey-Brown Group 199D.

Winter hardiness: Not tested.

I claim:

1. A new and distinct variety of rose plant of the shrub class, substantially as herein shown and described, characterized particularly by its soft pink blooms, touched with apricot in the form of shallow, incurved cups; upright, bushy shrub growth; and light myrrh fragrance.

* * * * *

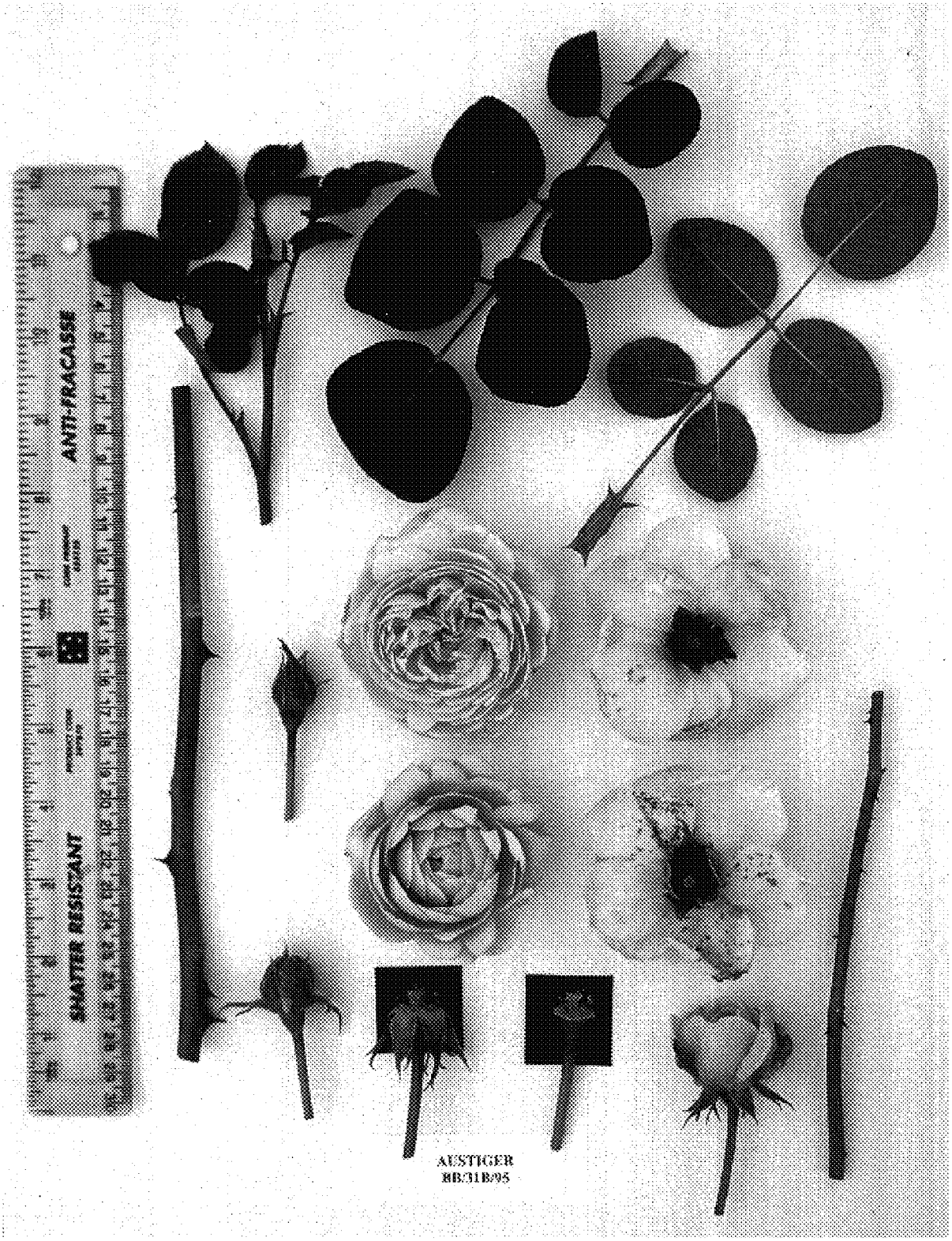
SHATTER RESISTANT
ANTI-FRACASSE
AUSTIGER
BB/31B/95